United States Patent
Kim et al.

(10) Patent No.: US 10,743,638 B2
(45) Date of Patent: *Aug. 18, 2020

(54) BEAUTY CARE PACK AND METHOD FOR MANUFACTURING SAME

(71) Applicant: AMOLIFESCIENCE CO., LTD., Seoul (KR)

(72) Inventors: Chan Kim, Gwangju (KR); Seung Hoon Lee, Paju-si (KR); Kyu Won Baek, Seoul (KR); Song Hee Koo, Seoul (KR); Ji Hyun Lee, Incheon (KR); Jun Keun Cho, Suwon-si (KR); Yong Sik Jung, Yongin-si (KR); Hyun Soo Park, Incheon (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 429 days.

This patent is subject to a terminal disclaimer.

(21) Appl. No.: 15/616,223

(22) Filed: Jun. 7, 2017

(65) Prior Publication Data

US 2017/0340090 A1 Nov. 30, 2017

Related U.S. Application Data

(63) Continuation-in-part of application No. PCT/KR2015/013357, filed on Dec. 8, 2015.

(30) Foreign Application Priority Data

Dec. 10, 2014 (KR) .................. 10-2014-0177682

(51) Int. Cl.
*A45D 44/00* (2006.01)
*A61Q 19/00* (2006.01)
(Continued)

(52) U.S. Cl.
CPC .......... *A45D 44/002* (2013.01); *A61K 8/0212* (2013.01); *A61K 8/19* (2013.01);
(Continued)

(58) Field of Classification Search
CPC .... A45D 44/002; A61Q 19/08; A61Q 19/007; A61Q 19/00; D01D 5/0023;
(Continued)

(56) References Cited

U.S. PATENT DOCUMENTS 10,143,292 B2 * 12/2018 Kim .................. A45D 44/22
2015/0272855 A1 * 10/2015 Kim .................. A45D 34/04
424/401

FOREIGN PATENT DOCUMENTS

JP 2000119128 4/2000
JP 2013119676 6/2013
(Continued)

OTHER PUBLICATIONS

Papakonstantinou, et al. (NPL: Dermatoendocrinol., vol. 4(3), pp. 253-258, Jul. 1, 2012).*
(Continued)

*Primary Examiner* — Blessing M Fubara
(74) *Attorney, Agent, or Firm* — Cantor Colburn LLP

(57) ABSTRACT

Provided is a beauty care pack including a release film and a beauty care sheet which is separably attached to the release film, wherein the beauty care sheet comprises: a support; a fiber layer which is laminated on the support and in which water-soluble polymers are formed in the form of a nano-fiber web; a moisturizing layer which is laminated on the fiber layer and consists of the water-soluble polymers and moisturizing materials; and a beauty care layer which is laminated on the moisturizing layer and in which the water-soluble polymers and functional materials are formed in the
(Continued)

form of a nanofiber web, such that active ingredients are absorbed into the skin while being dissolved by moisture.

15 Claims, 11 Drawing Sheets

(51) Int. Cl.
*A61Q 19/08* (2006.01)
*A61K 8/02* (2006.01)
*A61K 8/19* (2006.01)
*A61K 8/46* (2006.01)
*A61K 8/65* (2006.01)
*A61K 8/67* (2006.01)
*A61K 8/73* (2006.01)
*A61K 8/81* (2006.01)
*A61K 8/87* (2006.01)
*D01D 5/00* (2006.01)
*A61M 35/00* (2006.01)
*D01F 4/00* (2006.01)
*D01F 6/52* (2006.01)

(52) U.S. Cl.
CPC ............ *A61K 8/466* (2013.01); *A61K 8/65* (2013.01); *A61K 8/678* (2013.01); *A61K 8/735* (2013.01); *A61K 8/8129* (2013.01); *A61K 8/8176* (2013.01); *A61K 8/87* (2013.01); *A61Q 19/00* (2013.01); *A61Q 19/007* (2013.01); *A61Q 19/08* (2013.01); *D01D 5/0023* (2013.01); *A61K 2800/26* (2013.01); *A61K 2800/83* (2013.01); *A61M 35/10* (2019.05); *D01D 5/0038* (2013.01); *D01F 4/00* (2013.01); *D01F 6/52* (2013.01); *D10B 2211/06* (2013.01); *D10B 2321/06* (2013.01)

(58) Field of Classification Search
CPC ...... D01D 5/0038; A61K 8/87; A61K 8/8176; A61K 8/8129; A61K 8/735; A61K 8/678; A61K 8/65; A61K 8/466; A61K 8/19; A61K 8/0212; A61K 2800/83; A61K 2800/26; D01F 6/52; D01F 4/00; A61M 35/00; D10B 2321/06
See application file for complete search history.

(56) References Cited

FOREIGN PATENT DOCUMENTS

| | | |
|---|---|---|
| JP | 2014147463 | 8/2014 |
| KR | 200418839 | 6/2006 |
| KR | 20060091720 | 8/2006 |
| KR | 20110080066 | 7/2011 |
| KR | 20120005443 | 1/2012 |
| KR | 20120133334 | 12/2012 |
| KR | 20130057849 | 6/2013 |
| KR | 20140052639 | 5/2014 |
| KR | 20140091449 | 7/2014 |

OTHER PUBLICATIONS

Machine translation of KR 200418839 to Park, Jun. 14, 2006.*
International Search Report—PCT/KR2015/013357 dated Mar. 18, 2016.

* cited by examiner

BEAUTY CARE PACK AND METHOD FOR MANUFACTURING SAME

CROSS-REFERENCE TO RELATED APPLICATIONS

This application is a continuation of PCT Patent Application No. PCT/KR2015/013357 filed on Dec. 8, 2015, which claims priority to and the benefit of Korean Application No. 10-2014-0177682 filed on Dec. 10, 2014 and Korean Application No. 10-2015-0046230 filed on Apr. 1, 2015, in the Korean Patent Office, the entire contents of which are incorporated herein by reference.

TECHNICAL FIELD

The present invention relates to a beauty care pack (or a cosmetic pack) which is dissolved by moisture such as water when being attached to the skin so that nutrients are absorbed onto the skin, and a method of manufacturing the beauty care pack.

BACKGROUND ART

Conventional general beauty care packs have been manufactured to contain essence including nutrients such as natural extracts, proteins, and vitamins on a woven fabric or a nonwoven fabric so as to have functions such as whitening, wrinkle reduction, moisture supply, relief from skin troubles, and allowance of skin elasticity.

However, since the conventional beauty care packs are manufactured on the basis of a woven fabric or a nonwoven fabric, sufficient adhesion is not achieved at the interface contacting the skin, and thus effective ingredients cannot be sufficiently transferred to the deep part of the skin. In addition, an excessive amount of essence has been added to improve adhesive strength or power with respect to the skin.

Therefore, when a user makes an action actively with a conventional beauty care pack attached to the skin, the beauty care pack may fall or flow down due to the self-weight of the beauty care pack itself and the excessive essence may flow out, to thus result in uncomfortable and unpleasant feeling and also cause a loss of the essence. In addition, wearing a beauty care pack may often make it difficult for a wearer to take daily activities, and thus the wearer may have to lie down during the time of wearing the beauty care pack.

In order to overcome such disadvantages, hydrogel beauty care packs have recently been widely used. Since the hydrogel beauty care pack is excellent in the feeling of fit, a wearer who wears the hydrogel beauty care pack may perform daily activities, but the hydrogel beauty care pack is so thick to cause limited adhesion and to result in inconveniences of having to remove the hydrogel beauty care pack separately due to the flowing-down of the excessive essence or after the lapse of the wearing time.

Recently, nanofibers having a diameter of less than 1 μm have been actively studied using an electrospinning technique. These nanofibers are formed in a laminated structure having a three-dimensional pore structure at the same time of manufacture, and can provide a much larger skin contact area than conventional woven or nonwoven fabrics when used in the field of cosmetics. In addition, when manufacturing nanofibers, various functional materials are mixed with a spinning solution, and the spinning solution mixed with the various functional materials is spun, to then be manufactured in the form of nanofibers mounted with the functional materials.

As disclosed in Korean Patent Application Publication No. 10-2011-080066, a conventional beauty care pack has been proposed as a skin care pack, in which a double-layered nanofiber layer is formed on a nonwoven fabric, and the double-layered nanofiber layer is surface-treated with plasma. However, this technology includes a process of making a composite of the nanofiber layer on the nonwoven fabric and a secondary process such as a plasma treatment, to thus cause not only a problem of increasing a process cost, and but also cause inconveniences in wearing the beauty care pack and making an action due to the addition of the nonwoven fabric.

In addition, a process such as lamination, thermal bonding, or ultrasonic bonding using a chemical adhesive or the like is required to make a composite of the nonwoven fabric and the nanofiber layer. When the adhesive or the like is not used, peeling between the nonwoven fabric and the nanofiber layer may happen due to the functional essence or moisture.

Furthermore, the nanofibers of the double-layered structure are spun in the form of a core/shell, in which the core portion is made of polyurethane or the like, and the shell portion contacting the skin is made of biodegradable polymers to minimize the trouble with the skin. However, in the case that 100% of the residual solvent is not removed due to the use of the toxic solvent, there is a problem of secondary contamination by the residual solvent.

Particularly, since most of the biodegradable polymers used in the conventional art are required to be hydrophilized through a plasma treatment process due to the hydrophobic properties of the biodegradable polymers, there may have problems of causing an increase in the process cost as well as causing deterioration of the functional material.

DISCLOSURE

Technical Problem

Accordingly, it is an object of the present invention to provide a beauty care pack and a method of manufacturing the same, in which a water-soluble polymer and a functional material are simultaneously electrospun to thus obtain a nanofiber web containing the functional material, and the nanofiber web containing the functional material is used to allow effective ingredients to be absorbed into the skin while being melted by moisture.

It is another object of the present invention to provide a beauty care pack which is easily stored and packaged because a water-soluble polymer and a functional material can be simultaneously electrospun and manufactured into a dried sheet form, and which is conveniently used since a dried sheet of the beauty care pack is attached on the face of a user, and a method of manufacturing the same.

It is still another object of the present invention to provide a beauty care pack which can fundamentally prevent adverse effects on the skin such as skin troubles caused by organic solvents by using water as a solvent when the beauty care pack is prepared by electrospinning, and a method of manufacturing the same.

It is yet another object of the present invention to provide a beauty care pack having a moisturizing layer to further improve a moisturizing effect and a method of manufacturing the same.

It is still yet another object of the present invention to provide a beauty care pack having a mesh member on a support so that a functional material can be entirely absorbed by the skin without being left on the support, and a method of manufacturing the same.

It is a further object of the present invention to provide a beauty care pack which is formed to have a knob formed on a beauty care sheet in foldable type to prevent a cosmetic substance from staining the hand when a user holds the knob, and a method of manufacturing the same.

Technical Solution

According to an aspect of the present invention, there is provided a beauty care pack comprising: a release film; and a beauty care sheet which is separably attached to the release film, wherein the beauty care sheet comprises: a support; a fiber layer which is laminated on the support and in which water-soluble polymers are formed in the form of a nanofiber web; a moisturizing layer which is laminated on the fiber layer and made of water-soluble polymers and moisturizing materials; and a beauty care layer which is laminated on the moisturizing layer and in which the water-soluble polymers and functional materials are formed in the form of a nanofiber web.

Preferably but not necessarily, the support may be any one of PET (polyethylene terephthalate), PE (polyethylene), PP (polypropylene), woven fabrics, and nonwoven fabrics.

Preferably but not necessarily, the support may be formed in a netting thread shape by weaving a metal wire.

Preferably but not necessarily, the beauty care pack may further comprise a mesh member, wherein the mesh member may be made of any one of polyester, PET (polyethylene terephthalate), PE (polyethylene), PP (polypropylene), woven fabrics, and nonwoven fabrics, and may have a through-hole size of 0.1 to 10 mm.

Preferably but not necessarily, the fiber layer may be formed into a nanofiber web by electrospinning a spinning solution containing a water-soluble polymer, a solvent, and an additive.

Preferably but not necessarily, the moisturizing layer may be formed by electrospinning a spinning solution containing a water-soluble polymer, a solvent, and a moisturizing material.

Preferably but not necessarily, the beauty care pack may further comprise a protective film laminated on the beauty care layer to protect the beauty care layer.

Preferably but not necessarily, the beauty care layer may be formed into a nanofiber web by electrospinning a spinning solution that is obtained by dissolving a water-soluble polymer material, a functional material, and a crosslinking agent together in a solvent.

Preferably but not necessarily, the beauty care sheet may comprise an upper beauty sheet attached to an upper portion of a face and a lower beauty care sheet attached to a lower portion of the face, in which a nose portion surrounding the nose is formed to protrude from a lower end of the upper beauty care sheet, and a nose groove portion corresponding to the nose portion may be formed on the top of the lower beauty care sheet.

Preferably but not necessarily, a forehead line recessed inward may be formed at the center of the upper surface of the upper beauty care sheet, and a chin line recessed inward may be formed at the center of the lower surface of the lower beauty sheet.

Preferably but not necessarily, a separating knob is formed on a side surface of the beauty care sheet, in which the separating knob may comprises a first knob extended from a side surface of the beauty care sheet, and a second knob extended from the first knob and folded and covered on one side of the first knob.

Preferably but not necessarily, the second knob may have a fitting protrusion, and the first knob may have a fitting groove into which the fitting protrusion is fitted.

According to another aspect of the present invention, there is provided a method of manufacturing a beauty care pack, the method comprising the steps of: electrospinning a first spinning solution mixed with a water-soluble polymer onto a support, to thus form a fiber layer of a nanofiber web type; electrospinning a second spinning solution mixed with a water-soluble polymer and a moisturizing material onto the fiber layer to thus form a moisturizing layer; and electrospinning a third spinning solution mixed with the water-soluble polymer and a functional material onto the moisturizing layer to thus form a beauty care cosmetic layer in the form of a nanofiber web.

Advantageous Effects

The beauty care pack of the present invention uses a nanofiber web containing a functional material by simultaneous electrospinning of a water-soluble polymer and a functional material, thereby enabling effective ingredients to be absorbed into the skin while being melted by moisture, thus minimizing an amount of use of the functional material, and maximizing a beauty care effect.

The beauty care pack of the present invention can be manufactured in the form of a dried sheet by simultaneous electrospinning of a water-soluble polymer and a functional material, so that it is easy and convenient to store and pack it, and a dry sheet of the beauty care pack is attached to the face, so that it is convenient to use it.

The beauty care pack of the present invention can fundamentally prevent skin adverse effects such as skin troubles caused by organic solvents from being adversely affected on the skin by using water as a solvent when the beauty pack is prepared by electrospinning.

The beauty care pack of the present invention can further improve a moisturizing effect by providing a moisturizing layer.

The beauty care pack of the present invention includes a mesh member on a support so that a functional material can be entirely absorbed by the skin without causing the functional material to remain on the support.

The beauty care pack of the present invention may be formed of a knob as a foldable type formed on a beauty care sheet to prevent cosmetic substances from being put on the hands when a user holds the knob.

BEST MODE

Figure 1:
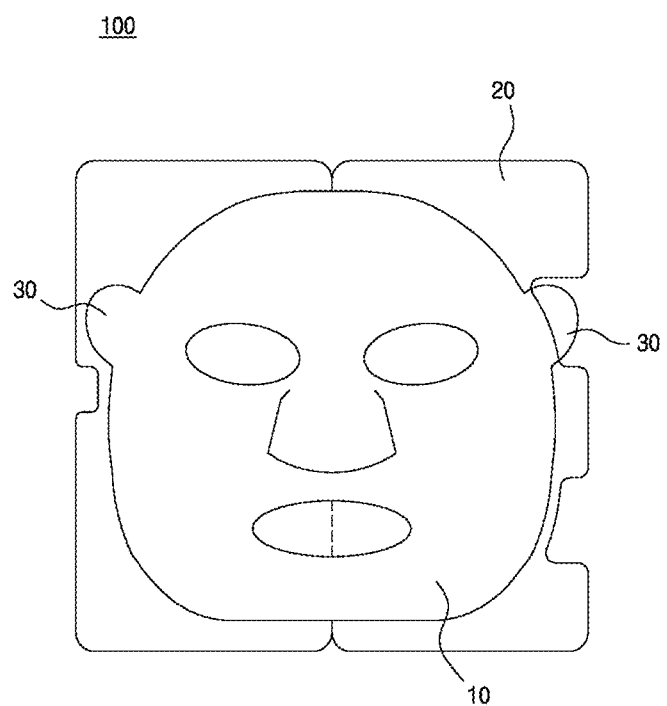
FIG. 1 is a plan view of a beauty care pack according to a first embodiment of the present invention.

Hereinafter, embodiments of the present invention will be described in detail with reference to the accompanying drawings. The sizes and shapes of the components shown in the drawings may be exaggerated for clarity and convenience. In addition, terms defined in consideration of the configuration and operation of the present invention may vary depending on the intention or custom of the user, the operator, and the like. Definitions of these terms should be based on the content of this specification.

As shown in FIG. 1, a beauty care pack 100 according to a first embodiment includes a release film 20, and a beauty care sheet 10 which is detachably attached to the release film 20, and is formed by electrospinning a water-soluble polymer and a functional material together, the beauty care sheet 10 being laminated with a plurality of layers.

Here, one or both of the release film 20 and the beauty care sheet 10 is provided with a separating knob (or knobs) 30 for allowing a user to hold by hand when separating the release film 20 and the beauty care sheet 10 from each other.

Figure 2:
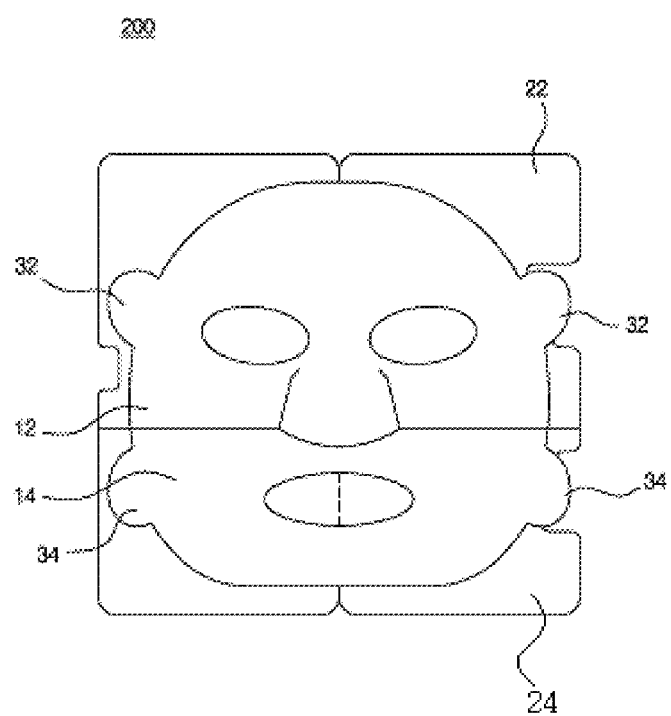
FIG. 2 is a plan view of a beauty care pack according to a second embodiment of the present invention.

As shown in FIG. 2, a beauty care pack 200 according to a second embodiment may include an upper beauty care sheet 12 attached to an upper portion of a face and having an upper knob (or knobs) 32 formed on one side thereof, a lower beauty care sheet 14 attached to a lower portion of the face and having a lower knob (or knobs) 34 formed on the other side thereof, an upper release film 22 detachably attached to the upper beauty sheet 12 and a lower release sheet 22 detachably attached to the upper beauty care sheet 12, and a lower release film 24 detachably attached to the lower beauty care sheet 14.

Figure 3:
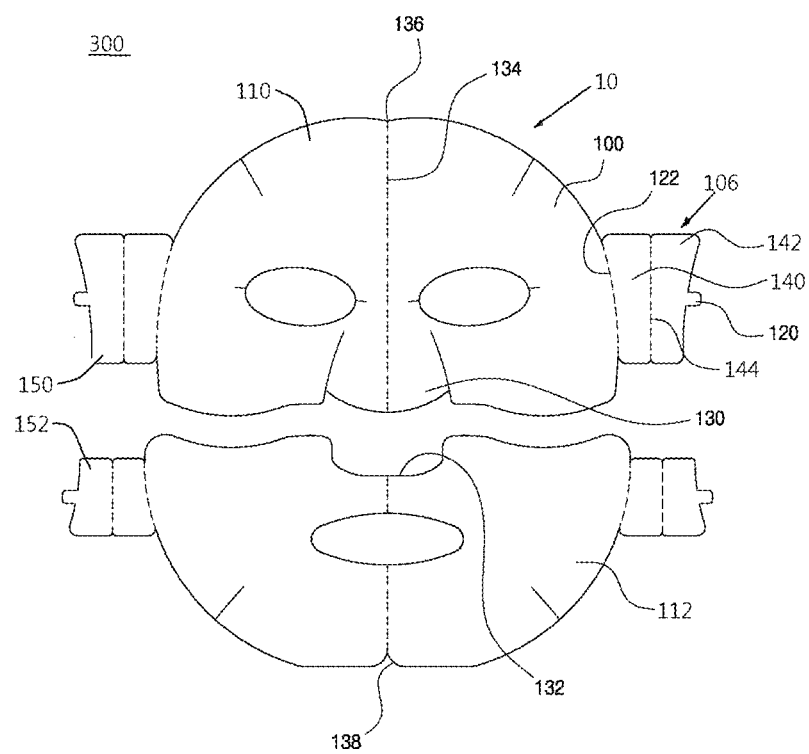
FIG. 3 is a plan view of a beauty care pack according to a third embodiment of the present invention.
Figure 4:
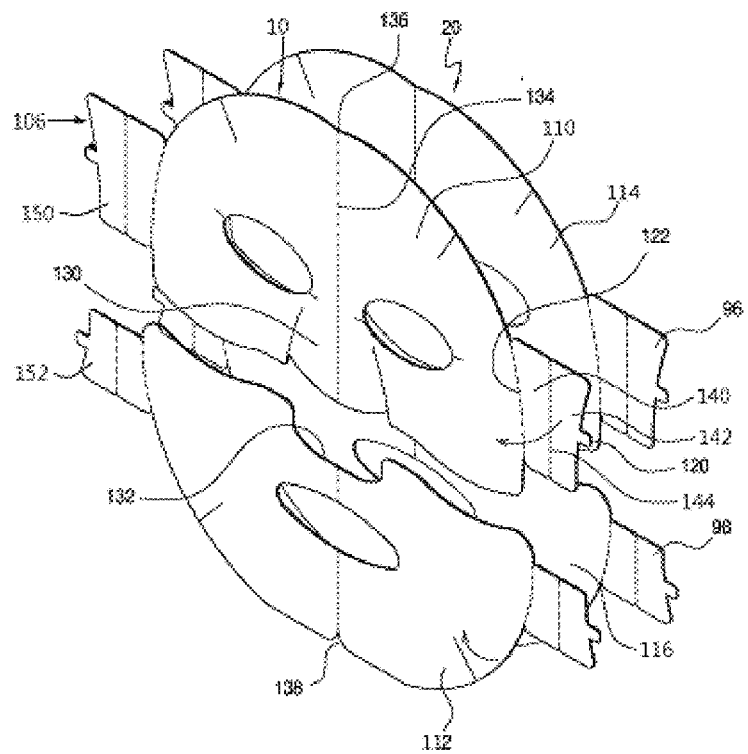
FIG. 4 is a perspective view of the beauty care pack according to the third embodiment of the present invention.

As shown in FIGS. 3 and 4, a beauty care pack 300 according to a third embodiment includes a beauty sheet 10, a release film 20 detachably attached to the beauty care sheet 10, and a separating knob (or knobs) 106 which is formed on one or both of the beauty care sheet 10 and the release film 20 and is caught by hand or hands when separating the release film 20 and the beauty sheet 10.

The beauty care sheet 10 includes an upper beauty care sheet 110 attached to an upper part of a face and a lower beauty care sheet 112 attached to a lower part of the face.

The upper beauty care sheet 110 and the lower beauty care sheet 112 are separated from each other around the nose in which a nose portion 130 is protruded from the lower end of the upper beauty care sheet 110, and a nose groove portion 132 corresponding to the nose portion 130 is formed. In addition, at the center of the upper beauty care sheet 110 and the lower beauty care sheet 112, a folding line 134 cut at regular intervals is formed so that the beauty care sheet 10 can be folded in half.

In addition, a forehead line 136 recessed inward is formed at the center of the upper surface of the upper beauty care sheet 110 and a chin line 138 recessed inward is formed at the center of the lower surface of the lower beauty care sheet 112 so that the beauty care sheet 10 of the present invention may be formed to match a facial shape of Asians.

The release film 20 includes an upper release film 114 detachably attached to the upper beauty care sheet 110 and a lower release film 116 detachably attached to the lower beauty care sheet 112.

When the beauty pack is attached to the face, the release film 20 is detached from the beauty care sheet 10. Here, the beauty sheet 10 may be damaged by touching the beauty sheet 10 by hand, or various germs in the hands may infiltrate the beauty sheet 10, and the beauty sheet 10 may be contaminated.

Therefore, in this embodiment, the separating knob (or knobs) 106 is formed on one side of the beauty care sheet 10, and when the release film 20 is separated from the beauty care sheet 10, the separating knob 106 is held by hand so that the separating operation is easy and simple, and the beauty care sheet 10 can be prevented from being damaged or contaminated.

The separating knob 106 includes a first knob or knobs 140 extending from one side or both sides of the beauty care sheet 10 and a second knob 142 extending from the first knob or knobs 140 and folded and covered on one side of the first knob or knobs 140.

A folding line 144 is formed between the first knob 140 and the second knob 142 in a cutting form at a predetermined interval so that the second knob 142 can be folded on the first knob 140. A fitting protrusion 120 protrudes from a side surface of the second knob 142 and a fitting groove 122 is formed in the first knob 140 so that the second knob 142 is folded to overlap the first knob 140, and then the fitting protrusion 120 is inserted into the fitting groove 122 to fix the overlapping state of the first knob 140 and the second knob 142.

When the separating knob 106 is folded so as to overlap the second knob 142 with the first knob 140, a support that supports the beauty care sheet 10 is disposed on the outer surface of the separating knob 106 and a beauty care layer containing a beauty care material is disposed on the inner surface of the separating knob 106. Thus, when the separating knob 106 is held by hand, the support is held by hand, to thereby prevent the beauty care material contained in the beauty care layer from staining the hand, and also to eliminate the possibility of contaminating the beauty care layer due to various germs that are stained in the hand.

The separating knob 106 includes an upper knob or knobs 150 formed on one side or both sides of the upper beauty care sheet 110 and a lower knob or knobs 152 formed on one side or both sides of the lower beauty care sheet 112.

The release film 20 is made of PET or the like and has strength enough to support the beauty care sheet 10. The upper release film 114 may be formed in the same shape as the upper beauty care sheet 110 and the lower release film 116 may be formed in the same shape as the lower beauty care sheet 112.

The upper release film 114 may be formed with an upper knob 96 having the same shape as that of the upper knob 150 formed on the upper beauty care sheet 110. The lower release film 116 may be formed with a lower knob 98 of the same type as that of the lower knob 152 formed on the lower beauty care 112.

The beauty care pack may be formed of a single beauty care pack attached to the entire face in addition to a structure separated into the upper and lower parts. In addition, the upper beauty care sheet and the lower beauty care sheet may be used individually. In addition to the beauty care pack of a mask pack type to be attached to the face, the beauty care pack can be used as a neck pad attached to the neck, a nose pack which is attached to the outer surface of the nose so as to remove the sebum of the nose and perform a cosmetic function of the nose, or an eye patch which is attached under eyes to remove wrinkles and remove dark circles.

In addition to the above kinds of the beauty care pack, the beauty care pack of the present invention may be formed in various forms that can absorb nutrients to the skin by being adhered to the body.

Figure 5:
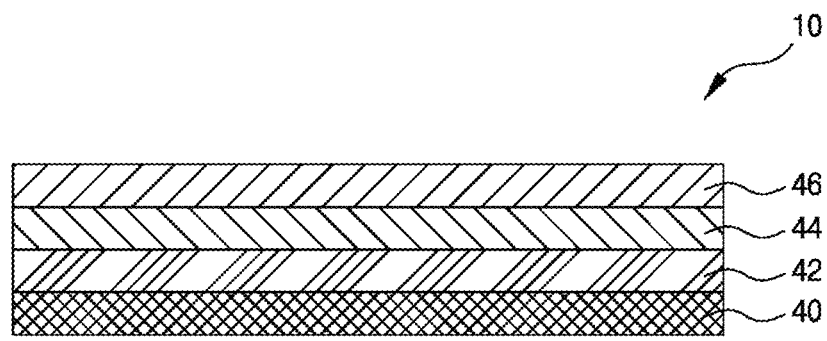
FIG. 5 is an enlarged cross-sectional view illustrating a beauty care sheet structure according to the first embodiment of the present invention.

FIG. 5 is a cross-sectional view of a beauty care sheet according to a first embodiment of the present invention.

As shown in FIG. 5, the beauty care sheet 10 according to the first embodiment includes a support 40 that serves to support the entire beauty care sheet 10, a fiber layer 42 that is formed in a nanofiber web shape by electrospinning a spinning solution which includes a water-soluble polymer in the support 40, a moisturizing layer 44 which is laminated on the fiber layer 42 and which is formed by electrospinning a spinning solution containing a moisturizing material, and a beauty care layer 46 which is laminated on the moisturizing layer 44 and which is formed in a nanofiber web shape by electrospinning a spinning solution containing a functional material.

The support 40 is formed of a mesh member having a plurality of throughholes having a predetermined diameter. Here, it is preferable that the throughhole size of the mesh member has a size such that the nanofiber web can be collected in the support 40 when the fiber layer 42 is electrospun onto the support 40. Specifically, the throughhole size of the mesh member may be 0.1 to 10 mm, preferably 0.1 to 5 mm.

The support 40 may be made of various materials capable of serving as a support for a beauty care sheet such as a silicon sheet, a PET sheet, a nonwoven fabric, a PE, a PP, and a PU in addition to the mesh member.

The support 40 may be formed in a netting thread shape by weaving yarn, fiber yarn, aluminum wire, or resin yarn. When the support 40 is in the form of a netting thread, the light can be reflected to provide a shiny effect, so that the design can be made beautiful.

The fiber layer 42 is formed by mixing a water-soluble polymer and a solvent at an appropriate ratio to prepare a spinning solution, then electrospinning the spinning solution to form nanofibers having a fiber diameter of less than 1 μm, and laminating the nanofibers so as to be formed into a nanofiber web shape having fine pores.

Here, the content of the water-soluble polymer is set to be in the range of 5 to 50 wt % based on the spinning solution, and the viscosity of the spinning solution is set to be relatively high so that the nanofiber web can be collected on the mesh member having the throughholes.

The moisturizing layer 44 is formed by mixing a water-soluble polymer, a moisturizing material, and a solvent at an appropriate ratio to prepare a spinning solution, electrospinning the spinning solution onto the fiber layer 42 such that the spinning solution is sprayed and formed on the fiber layer 42.

As the moisturizing material, glycerin can be used, and any material can be used as long as it is a functional material having a moisturizing function instead of glycerin.

Here, the content of the moisturizing material is set to be in the range of 5 to 80 wt %, preferably 5 to 50 wt %, relative to the water-soluble polymer, so that the moisturizing effect can be exerted.

The beauty care layer 46 is prepared by mixing a water-soluble polymer and a functional material in a solvent at a proper ratio to prepare a spinning solution, and then electrospinning the spinning solution to form nanofibers having a fiber diameter of less than 1 μm, and laminating the nanofibers so as to be formed into a nanofiber web having fine pores.

The content of the functional material is preferably in the range of 0.1 to 30 wt %, more preferably 0.1 to 10 wt %, based on the weight of the water-soluble polymer.

The use of water or alcohol as the solvent contained in the spinning solution for forming the fiber layer 42, the moisturizing layer 44 and the beauty care layer 46 can prevent skin troubles and the like caused by organic solvents and the like.

The spinning method that may be applied for the present invention may employ any one of general electrospinning, air-electrospinning (AES), electrospray, electrobrown spinning, centrifugal electrospinning, and flash-electrospinning.

In preparing the beauty care sheet 10, a crosslinking agent is mixed into the spinning solution for crosslinking of the water-soluble polymer. Generally, when dissolving a polymer material, it is preferable to prepare a spinning solution while heating and stirring the polymer material, cooling the spinning solution to room temperature, and then adding a crosslinking agent so that the crosslinking agent is added to the spinning solution in such a range that a crosslinking reaction does not occur.

Therefore, when preparing the beauty care layer 10 of the present invention, it is preferable that the addition of the crosslinking agent during the preparation of the spinning solution is performed in the final step after dissolving the water-soluble polymer in water or alcohol and adding the functional material in the dissolved result. The content of the crosslinking agent to be added is preferably in the range of 0.1 wt % to 2 wt %, with respect to the polymer. The crosslinking can be performed by a method such as hot air blowing, heat treatment calendering, UV irradiation, etc. The content and time of the crosslinking agent can be adjusted according to the purpose of use.

The water-soluble polymer material may employ synthetic polymers or natural polymers as a material that may be electrospun. The synthetic polymers or natural polymers may be used alone or in combination thereof, but any polymers that may be dissolved in water or alcohol to form nanofibers by electrospinning are not particularly limited.

Examples of such water-soluble polymer materials may include one selected from polymers including polyvinyl pyrrolidone (PVP), polyvinyl alcohol (PVA), polyethylene oxide (PEO), carboxyl methyl cellulose (CMC), starch, polyacrylic acid (PAA), and hyaluronic acid, or a mixture of two or more thereof.

One of ingredients (such as albutine, niacinamide, and ascorbyl glucoside) that help skin whitening, ingredients (such as retinol and adenosine) that help to improve skin wrinkles, ingredients (such as titanium dioxide) that help to block ultraviolet rays, an antioxidant component, and an antibacterial component, or a mixture of two or more thereof, may be used as the functional material.

In addition, the functional material may comprise one or a mixture of two or more selected from water-soluble collagen, vegetable platinum, tocopherol, xylitol and plant extract.

The crosslinking agent or co-crosslinking agent may be formed of one selected from para-toluene sulfonic acid (TSA), polyurea-co-formaldehyde, tri-methylpropane trimethacrylate (TMPTMA), divinylbenzene (DVB), N-(1-hydroxy-2,2-dimethoxyethyl) acrylamide, N,N'-methylenebisacrylamide, ethylene glycol diacrylate, di(ethylene glycol) diacrylate, boric acid, and glutaraldehyde, or a mixture of two or more thereof.

Figure 6:
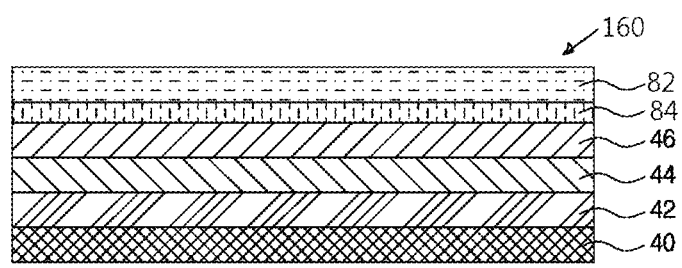
FIG. 6 is an enlarged cross-sectional view illustrating a beauty care sheet structure according to the second embodiment of the present invention.

As shown in FIG. 6, the beauty care sheet 10 according to the second embodiment includes a support 40 that serves to support the entire beauty care sheet 10, a fiber layer 42 that is formed in a nanofiber web shape by electrospinning a spinning solution which includes a water-soluble polymer in the support 40, a moisturizing layer 44 which is laminated on the fiber layer 42 and which is formed by electrospinning a spinning solution containing a moisturizing material, a beauty care layer 46 which is laminated on the moisturizing layer 44 and which is formed in a nanofiber web shape by electrospinning a spinning solution containing a functional material, and a protective film 82 which is attached by an adhesive layer 84 and protects the beauty care layer 46.

The protective film 82 may be formed of a PET film and is detachably attached to the beauty care layer 46 by the adhesive layer 84. The protective film 82 may be detached from the beauty care layer 46 when the beauty sheet 10 is attached to the face or may be detached from the beauty care layer 46 when the beauty care sheet 10 is attached to the release film 20.

Figure 7:
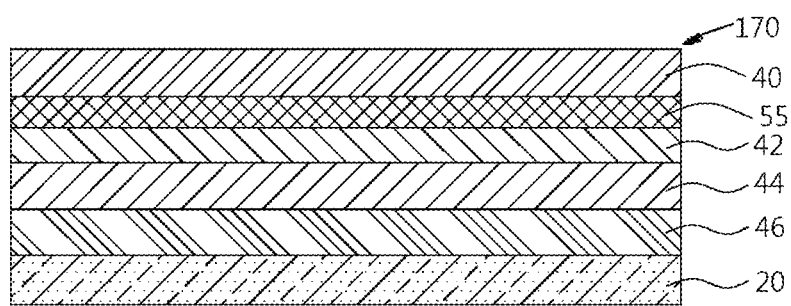
FIG. 7 is an enlarged cross-sectional view illustrating a beauty care sheet structure according to the third embodiment of the present invention.

As shown in FIG. 7, the beauty care sheet 170 according to the third embodiment includes a support 40 that serves to support the entire beauty care sheet 10, a mesh member 55 that is stacked on the support 40, a fiber layer 42 formed in a nanofiber web shape by electrospinning a spinning solution containing a water-soluble polymer in the mesh member 55, a moisturizing layer 44 which is laminated on the fiber layer 42 and which is formed by electrospinning a spinning solution containing a moisturizing material, and a beauty care layer 46 which is laminated on the moisturizing layer 44 and which is formed in a nanofiber web shape by electrospinning a spinning solution containing a functional material.

The support 40 according to the third embodiment has the same structure as the support 40 described in the first embodiment.

It is preferable that the throughhole size of the mesh member 55 be a size that the nanofiber web can be collected when the fiber layer 42 is electrospun to the mesh member 55. Specifically, the throughhole size of the mesh member 55 may be 0.1 to 10 mm, preferably 0.1 to 5 mm.

The mesh member 55 functions to smoothly stack the fiber layer, the moisturizing layer, and the beauty care layer on the support, and to allow the functional material to be completely absorbed by the skin without being left on the support 40.

The fiber layer 42, the moisturizing layer 44 and the beauty care layer 46 according to the third embodiment have the same structures as the fiber layer 42, the moisturizing layer 44 and the beauty care layer 46 described in the first embodiment.

The manufacturing process of the beauty care sheet will be described below.

Figure 8:
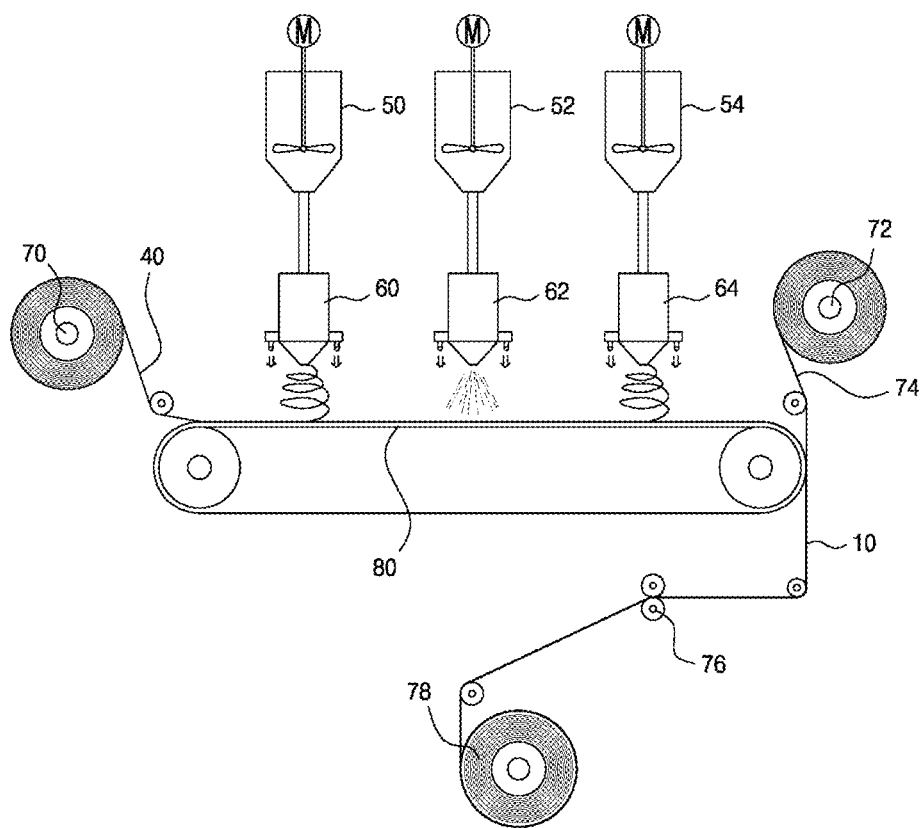
FIG. 8 is a schematic configuration diagram of an electrospinning apparatus for manufacturing a beauty care pack according to an embodiment of the present invention.
Figure 9:
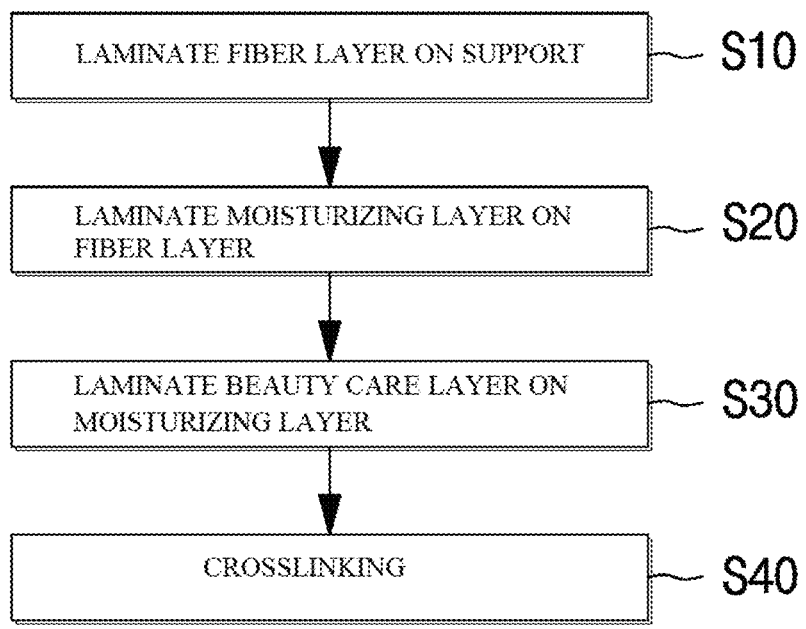
FIG. 9 is a flow chart showing a process of manufacturing a beauty care sheet according to the present invention.

FIG. 8 is a structural view of an apparatus for manufacturing a beauty care sheet according to the present invention, and FIG. 9 is a flowchart showing a method of manufacturing a beauty care sheet according to the present invention.

The apparatus for producing a beauty care sheet according to the present invention comprises a first storage tank 50 storing a first spinning solution in which a water-soluble polymer and a solvent are mixed, a second storage tank 52 storing a second spinning solution in which a water-soluble polymer, a moisturizing material and a solvent are mixed, a third storage tank 54 for storing a third spinning solution in which a water-soluble polymer, a functional material and a solvent are mixed, a first spinning nozzle 60 connected to a high-voltage generator and connected to the first storage tank 50 to form a fiber layer 42, a second spinning nozzle 62 connected to the high voltage generator and connected to the second storage tank 52 to form a moisturizing layer 44, and a third spinning nozzle 64 connected to the high voltage generator and connected to the third storage tank 54 to form a beauty care layer 46.

The first spinning nozzle 60, the second spinning nozzle 62 and the third spinning nozzle 64 are sequentially arranged at intervals to form the fiber layer 42, the moisturizing layer 44, and the beauty care layer 46 so as to be stacked in this order.

A collector 80 is provided below the spinning nozzles 60, 62 and 64 in which the fiber layer 42, the moisturizing layer 44 and the beauty care layer 46 are sequentially laminated. The nanofibers are emitted from the spinning nozzles 60, 62 and 64, by applying a high voltage electrostatic force of 90 to 120 KV between the collector 80 and each of the spinning nozzles 60, 62 and 64, and the nanofibers are accumulated in the collector 80 to form a nanofiber web.

A first roll 70 for feeding the support 40 to the collector 80 is disposed in front of the collector 80. A second roll 72 for laminating the protective layer 74 on the beauty care sheet 74 formed of a plurality of layers, a pressing roller 76 for pressing the beauty care sheet 10, and a third roll 78 for winding the completed beauty care sheet are disposed on the rear side of the collector 80.

Hereinafter, a process of manufacturing a beauty care sheet using the beauty care sheet producing apparatus constituted as described above will be described.

First, when the collector 80 is driven, the support 40 wound around the first roll 70 is supplied to the upper surface of the collector 80.

The support 40 is formed of a mesh member having a plurality of throughholes, and the throughhole size of the mesh member is set such that the nanofibers formed by electrospinning can be collected on the upper surface of the mesh member without flowing into the throughholes.

By applying a high voltage electrostatic force between the collector 80 and the first spinning nozzle 60, the first spinning nozzle 60 emits the first spinning solution to the support 40 in the form of nanofibers. Then, nanofibers are accumulated in the support 40 to form a fiber layer 42 in the form of a nanofiber web (S10).

Here, the content of the water-soluble polymer contained in the first spinning solution may be set in the range of 5 to 50 wt % so that the nanofiber web can be collected on the mesh member having the throughholes.

When the fiber layer 42 is completed, the collector 80 is driven so that the fiber layer 42 is moved to the lower portion of the second spinning nozzle 62 and the second spinning nozzle 62 electrospins the second spinning solution by applying a high voltage electrostatic force between the collector 80 and the second spinning nozzle 62. Then, the second spinning solution is sprayed onto the fiber layer 42 in a spray mode to form the moisturizing layer 44 (S20).

Here, the content of the moisturizing material contained in the second spinning solution is set to be in the range of 5 to 80 wt % relative to the water-soluble polymer so that sufficient moisture retention can be exhibited.

When the moisturizing layer 44 is completed, the collector 80 is driven so that the moisturizing layer 44 is moved to the lower portion of the third spinning nozzle 64 and the third spinning nozzle 64 electrospins the third spinning solution by applying a high voltage electrostatic force between the collector 80 and the third spinning nozzle 64. Then, nanofibers are accumulated in the support 40 to form the beauty care layer 46 in the form of a nanofiber web (S30).

Here, the content of the functional material contained in the third spinning solution may be set in the range of 0.1 to 30 wt %, relative to the water-soluble polymer, so that the beauty care effect can be exerted.

The protective film 82 for protecting the beauty care layer 46 may be laminated on the beauty care layer 46.

In order to adjust the time for the beauty care sheet 10 to be melted by moisture or mist, crosslinking is performed and a thermocompression bonding process is performed to increase a bonding force between the nanofibers (S40).

The crosslinking is controlled so that the complete crosslinking or the partial crosslinking proceeds to be self-melt over time by moisture, mist, or the like. The crosslinking can be carried out before or after thermocompression or calendering, or can proceed simultaneously with calendering. In addition, for partial crosslinking, the type and content of the crosslinking agent in the spinning solution, and hot air, heat treatment conditions, and UV irradiation or time can be adjusted.

In this case, it is preferable to carry out partial crosslinking in the range that the deterioration or destruction of the functional material does not occur, within the range of 80-100° C. for 30 minutes or less, but in the case of the heating and calendering at 150° C., partial crosslinking is carried out for 30 seconds or less, and is preferably executed in the range that the deterioration of the functional material and the partial crosslinking proceeds.

Then, the finished beauty care sheet 10 is wound on the third roll 78.

Hereinafter, the present invention will be described in more detail with reference to embodiments. However, the following embodiments are intended to further illustrate the present invention, and the scope of the present invention is not limited by these embodiments.

Embodiment 1

Polyvinyl alcohol (PVA) as a water-soluble polymer was mixed with water to become a concentration of 25 wt % and completely dissolved at 80° C. to prepare a spinning solution. Water-soluble collagen was added to the prepared spinning solution by 10 wt % relative to PVA and stirred at room temperature to prepare a final spinning solution. The final spinning solution was moved to a spinning pack and electrospinning was carried out in an electrospinning environment such as temperature of 30° C. and relative humidity of 60% under the circumstance that the applied voltage was 25 kV, the distance between the spinning nozzle and a current collector was 20 cm, and the discharge amount was 0.05 cc/g·hole/min, to thus obtain a nanofiber web.

Figure 10:
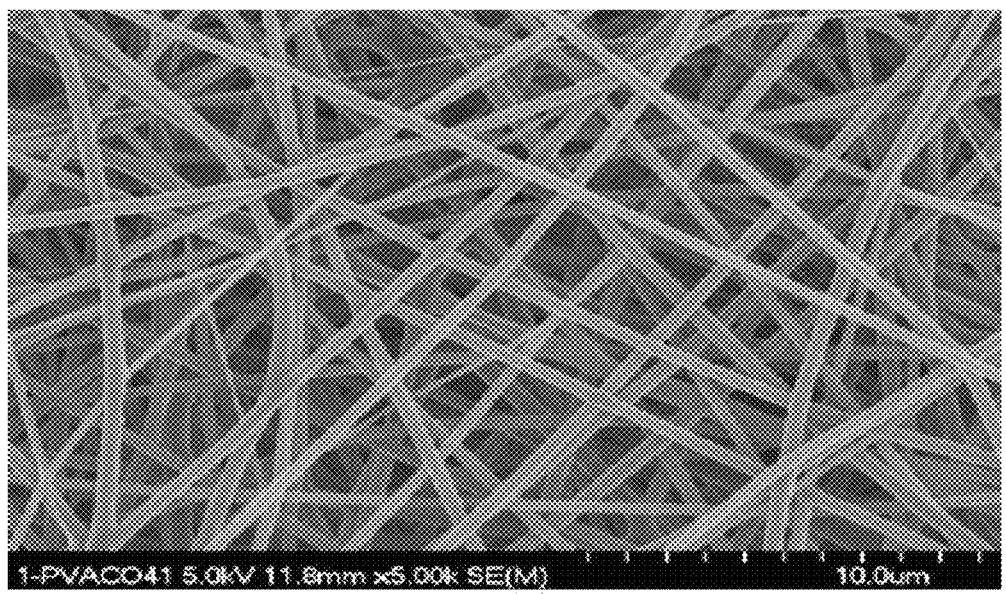
FIG. 10 is a scanning electron microscope (SEM) image of a PVA nanofiber web prepared according to the present invention.

A scanning electron microscope (SEM) image of the obtained PVA nanofiber web was shown in FIG. 10, and the distribution of the fiber diameter was in the range of about 150-350 nm and the average fiber diameter was about 200 nm. The PVA nanofiber web thus prepared was treated with a hot air furnace at 100° C. for 10 minutes to conduct partial crosslinking.

Embodiment 2

Polyvinyl alcohol (PVA) as a water-soluble polymer was dissolved in water at 25 wt % and completely dissolved at 80° C. Then, para-toluene sulfonic acid (TSA) as a crosslinking agent and water-soluble collagen as a functional material were added to PVA in an amount of 2 wt % and 5 wt %, respectively, relative to PVA, to thus prepare a spinning solution.

The spinning solution was spun in the same manner as in Embodiment 1 to obtain a PVA nanofiber web containing a crosslinking agent and water-soluble collagen.

Figure 11:
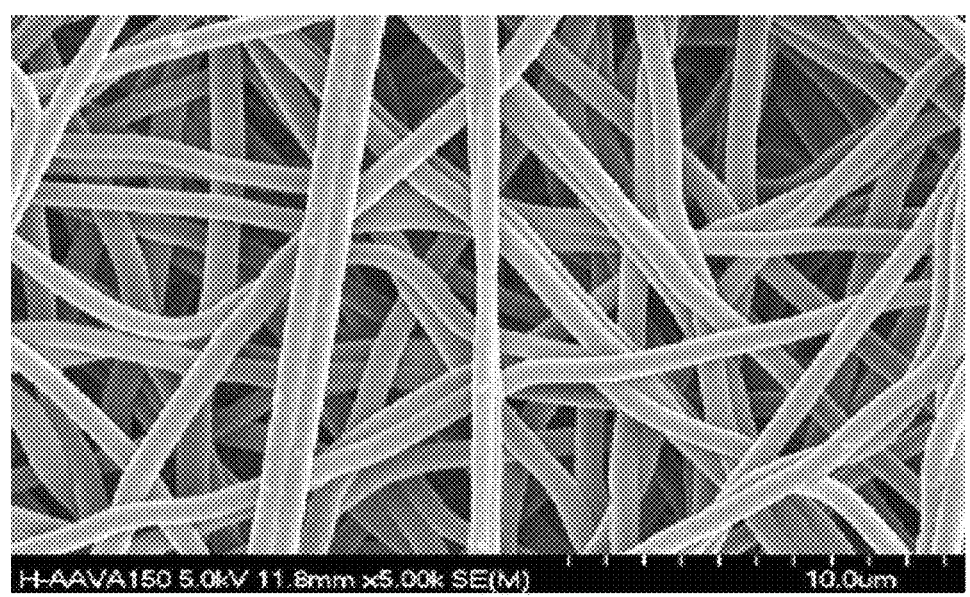
FIG. 11 is a scanning electron microscope (SEM) image of a fully crosslinked PVA nanofiber web according to an embodiment of the present invention.

The obtained PVA nanofibers were completely crosslinked by treatment with a hot air furnace at 150° C. for 30 minutes, and it was visually confirmed that the surfaces of the crosslinked PVA nanofibers changed from white to yellow as the crosslinking progressed. FIG. 11 shows a scanning electron microscope (SEM) image of the crosslinked nanofiber web according to this embodiment. As shown in FIG. 11, it was confirmed that fusion between the fibers occurred by the crosslinking treatment.

Embodiment 3

Polyvinyl pyrrolidone (PVP such as K-80) as a water-soluble polymer was mixed in a mixed solvent of ethanol and water (mixing ratio 75/25 wt %) so as to be 15 wt % and dissolved at room temperature to prepare a spinning solution. Water-soluble collagen, hyaluronic acid, and vegetable platinum were added to the prepared spinning solution in an amount of 5 wt %, respectively, relative to the PVP, and while stirring the spinning solution at room temperature, poly (urea-co-formaldehyde) as a crosslinking agent, was added to the spinning solution in an amount of 2 wt %, relative to the PVP, to thus prepare a final spinning solution.

The final spinning solution was electrospun in the same manner as in Embodiment 1 to obtain a nanofiber web containing PVP and a functional material. The obtained nanofibers were crosslinked in a hot air furnace at 125° C. for 30 minutes to obtain a PVP crosslinked nanofiber web containing a functional material.

Figure 12:
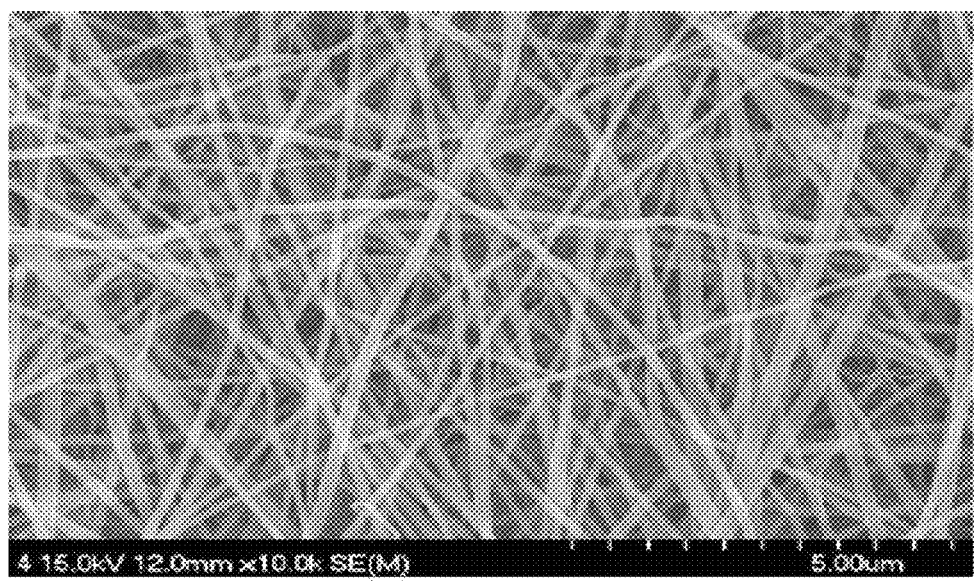
FIG. 12 is a scanning electron microscope (SEM) image of a PVA nanofiber web prepared according to an embodiment of the present invention.

Meanwhile, in the same manner as in Example 1, a nanofiber web composed of PVP alone in which a functional material was not mounted was prepared. SEM images of the obtained nanofiber web were shown in FIG. 12, and the average fiber diameter was in the range of 70-80 nm.

Figure 13:
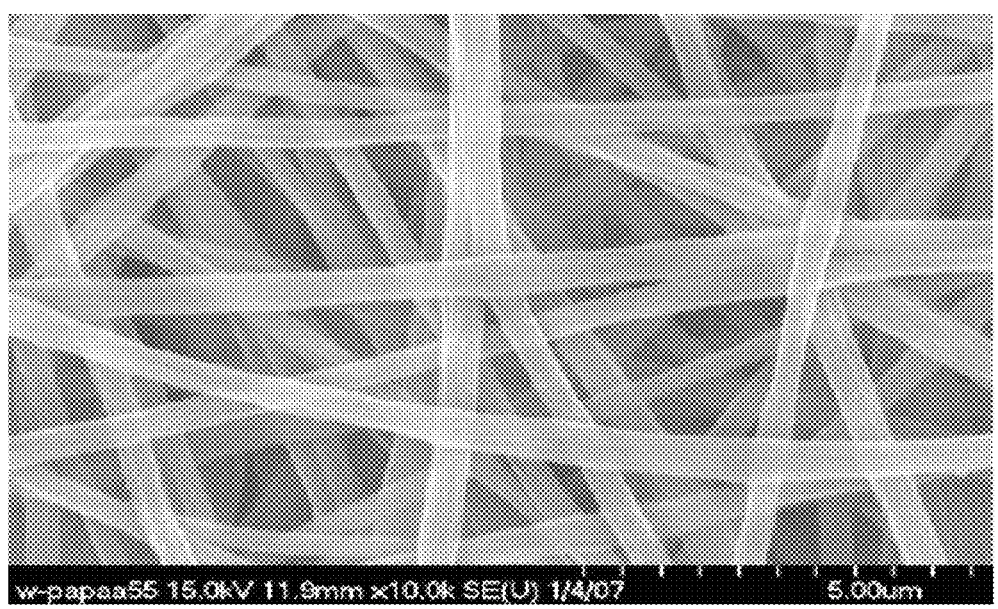
FIG. 13 is a scanning electron microscope (SEM) image of a PVP nanofiber web loaded with a functional material according to the present invention.

FIG. 13 is a scanning electron microscope (SEM) image of a PVP on which a functional material is mounted according to Embodiment 3, and it can be confirmed that the fiber diameter is significantly increased as compared with PVP alone.

Embodiment 4

A mixture of PVA and PVP as a water-soluble polymer in a ratio of 50:50 wt % was mixed with a mixed solvent of water and ethanol in a ratio of 75:25 wt %, and stirred at a temperature of 60° C. to prepare a primary spinning solution. After cooling the prepared primary spinning solution to room temperature, water-soluble collagen, hyaluronic acid, vegetable platinum and tocopherol were mixed as a functional material in an amount of 3 wt %, respectively, relative to the polymer to prepare a secondary spinning solution.

The crosslinking agent such as TSA was added to the prepared secondary spinning solution in an amount of 1 wt % relative to PVA and stirred to thus prepare a final spinning solution. The same procedure as in Embodiment 1 was followed to conduct electrospinning so that the content of the nanofibers was 20 gsm and calendered for a contact time of 10 seconds using a calender roll heated at 150° C. to thus perform partial crosslinking.

Figure 14:
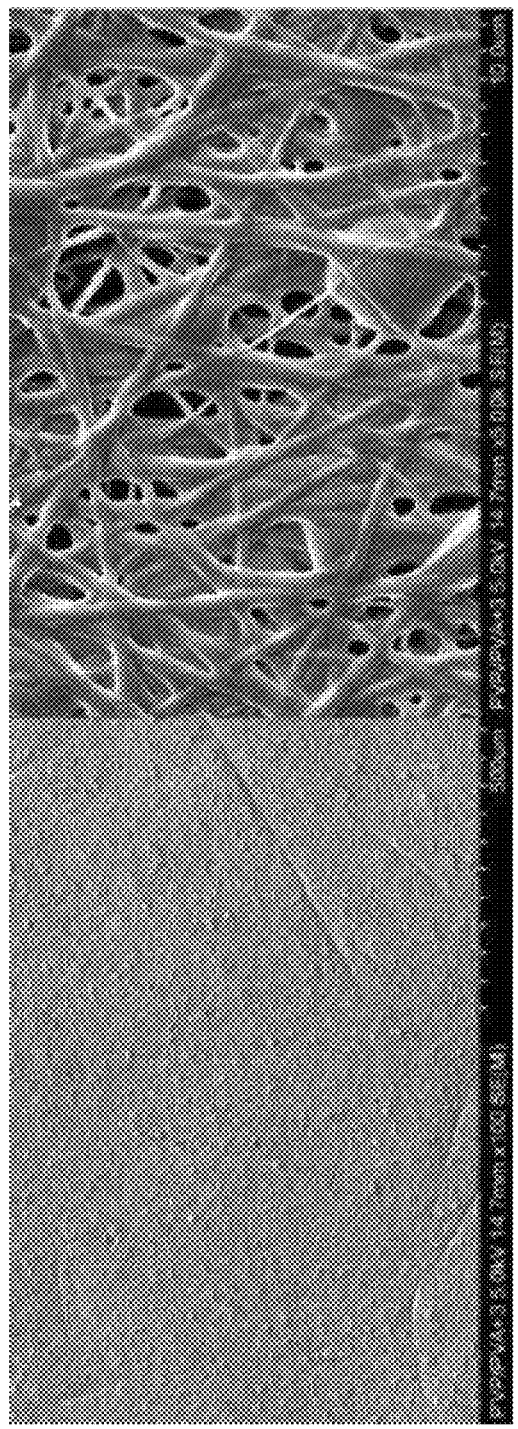
FIG. 14 is a scanning electron microscope (SEM) image of a PVA/PVP composite nanofiber web prepared according to the present invention, (a) with 100 times magnification, and (b) with 5,000 times magnification.

(a) and (b) of FIG. 14 are scanning electron microscope (SEM) images of a nanofiber containing a functional material in a PVA/PVP composite polymer according to Embodiment 4, with 100 times magnification and 5,000 times magnification, respectively, and it can be confirmed that fusion between the nanofibers is caused by partial crosslinking and calendering.

Embodiment 5

The crosslinking degree of the PVA/PVP nanofiber web prepared in Embodiment 4 was measured through calendering. (a) of FIG. 15 is a photograph of a PVA/PVP nanofiber web prepared according to a contact time of 3 seconds at a temperature of 150° C., (c) of FIG. 15 according to a contact time of 10 seconds, and (c) of FIG. 15 according to a contact time of 30 seconds.

Figure 15:
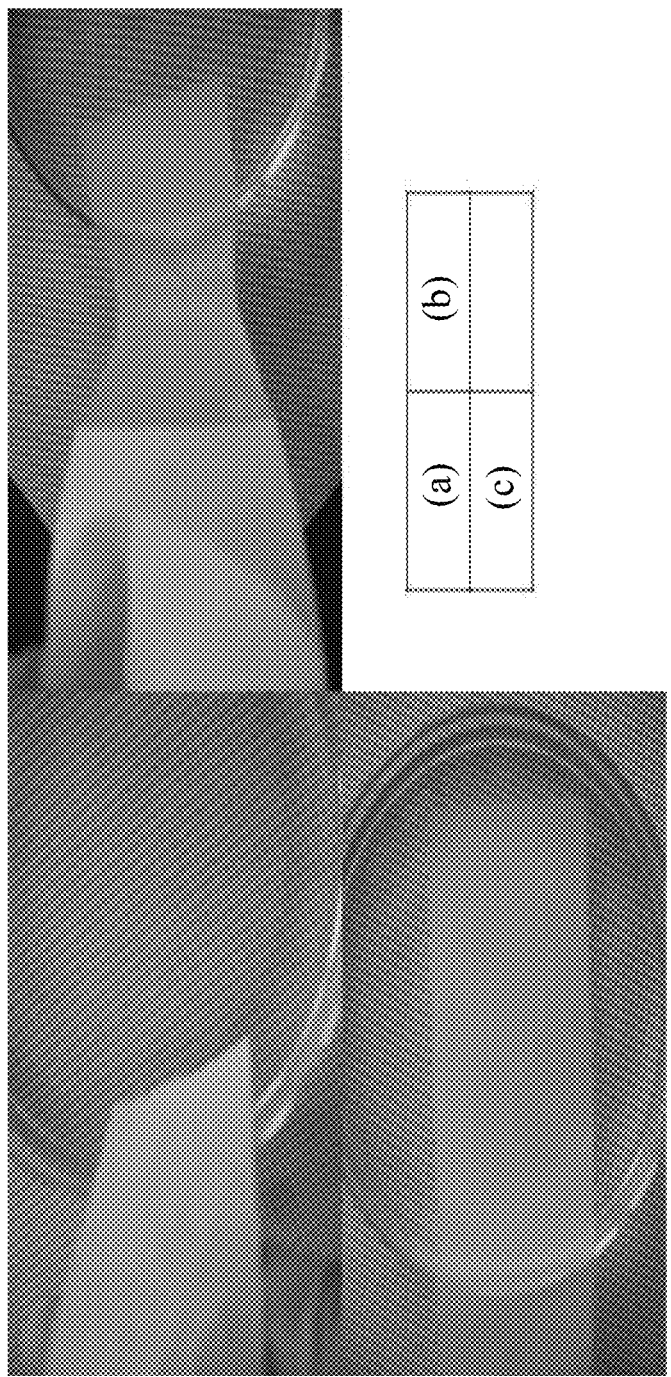
FIG. 15 is a photograph showing a degree of dissolution in water according to a contact time (a) of 3 seconds during heating and calendering of a PVA/PVP nanofiber web prepared according to an embodiment of the present invention, (b) of 10 seconds, and (c) of 30 seconds.

As shown in (a), (b) and (c) of FIG. 15, it can be seen that the crosslinking degree increases with an increase in the contact time at the time of calendering the hot plate. As shown in (a) of FIG. 15, when the contact time is short, the crosslinking does not proceed and it is confirmed that the nanofibers are melted simultaneously with a contact to water due to the large specific surface areas of the nanofibers. As shown in (b) and (c) of FIG. 15, it can be confirmed that when crosslinking proceeds, even if the nanofibers are in contact with water, the nanofibers do not melt immediately and absorb moisture.

From these results, it can be seen that, when using the beauty care sheet comprising the nanofiber web of the present invention, the skin is moisturized or the mist is dispersed to the skin, and then the beauty care sheet is attached to the skin, there is an effect that effective ingredients can be appropriately transmitted to the skin for a desired time through crosslinking.

What is claimed is:
1. A beauty care pack comprising:
a release film; and
a beauty care sheet which is separably attached to the release film,
wherein the beauty care sheet comprises:
a support;
a fiber layer which is laminated on the support, wherein the fiber layer is formed of first electrospun nanofibers in a form of a first porous nanofiber web, and the first electrospun nanofibers comprise a first water-soluble polymer;
a moisturizing layer which is laminated on the fiber layer, wherein the moisturizing layer is formed of a second water-soluble polymer and a moisturizing material; and
a beauty care layer which is laminated on the moisturizing layer and separably attached to the release film, wherein the beauty care layer is formed of second electrospun nanofibers in a form of a second porous nanofiber web, and the second electrospun nanofibers comprise a third water-soluble polymer and a functional material.

2. The beauty care pack of claim 1, wherein the support is formed of any one selected from the group consisting of PET (polyethylene terephthalate), PE (polyethylene), PP (polypropylene), woven fabrics, and nonwoven fabrics.

3. The beauty care pack of claim 1, wherein the support is formed of a metal wire mesh.

4. The beauty care pack of claim 1, further comprising: a mesh member laminated on the support.

5. The beauty care pack of claim 4, wherein the mesh member is made of any one selected from the group consisting of polyester, PET (polyethylene terephthalate), PE (polyethylene), PP (polypropylene), woven fabrics, and nonwoven fabrics, and has a throughhole size of 0.1 to 10 mm.

6. The beauty care pack of claim 4, wherein the support and the mesh member are laminated with an adhesive, wherein the adhesive is a hot-melt web.

7. The beauty care pack of claim 1, wherein the first electrospun nanofibers further comprise: an additive.

8. The beauty care pack of claim 1, wherein the fiber layer is formed of an opaque layer.

9. The beauty care pack of claim 1, further comprising: a protective film laminated on the beauty care layer to protect the beauty care layer.

10. The beauty care pack of claim 1, wherein the third water-soluble polymer material comprises: one selected from the group consisting of polyvinyl alcohol (PVA), polyvinyl pyrrolidone (PVP), polyethylene oxide (PEO), carboxyl methyl cellulose (CMC), starch, polyacrylic acid (PAA), hyaluronic acid, and a mixture of two or more thereof.

11. The beauty care pack of claim 1, wherein the functional material comprises: one or a mixture of two or more selected from the group consisting of water-soluble collagen, vegetable platinum, tocopherol, xylitol and plant extract.

12. The beauty care pack of claim 1, wherein the beauty care sheet comprises: an upper beauty care sheet capable of being attached to an upper portion of a user face and a lower beauty care sheet capable of being attached to a lower portion of the user face, and wherein the upper beauty care sheet comprises: a nose portion protruding from a lower end of the upper beauty care sheet, and the lower beauty care sheet comprises: a nose groove portion formed on top of the lower beauty care sheet.

13. The beauty care pack of claim 12, wherein the upper beauty care sheet comprises: a forehead line recessed inward at a center of an upper end portion of the upper beauty care sheet, and the lower beauty care sheet comprise: a chin line recessed inward at a center of a lower end portion of the lower beauty care sheet.

14. The beauty care pack of claim 1, wherein a separating knob is formed on a side surface of the beauty care sheet, and wherein the separating knob comprises: a first knob extended from the side surface of the beauty care sheet, and a second knob extended from the first knob and folded covering one side of the first knob.

15. The beauty care pack of claim 14, wherein the second knob has a fitting protrusion, and the first knob has a fitting groove into which the fitting protrusion is fitted.

\* \* \* \* \*